(12) United States Patent
Baratella et al.

(10) Patent No.: US 9,845,289 B2
(45) Date of Patent: Dec. 19, 2017

(54) PROCESS FOR THE SYNTHESIS OF DAPSONE AND ITS INTERMEDIATES

(71) Applicant: SEEGPHARM SA, Lugano (CH)

(72) Inventors: Marco Baratella, Lugano (CH); Graziano Castaldi, Lugano (CH); Marta Castaldi, Lugano (CH); Mauro Gaboardi, Lugano (CH); Giuseppe Pallanza, Lugano (CH)

(73) Assignee: SEEGPHARM SA, Lugano (CH)

( * ) Notice: Subject to any disclaimer, the term of this patent is extended or adjusted under 35 U.S.C. 154(b) by 0 days.

(21) Appl. No.: 15/328,267

(22) PCT Filed: Jul. 29, 2015

(86) PCT No.: PCT/EP2015/067411
§ 371 (c)(1),
(2) Date: Jan. 23, 2017

(87) PCT Pub. No.: WO2016/016321
PCT Pub. Date: Feb. 4, 2016

(65) Prior Publication Data
US 2017/0217883 A1    Aug. 3, 2017

Related U.S. Application Data

(60) Provisional application No. 62/032,154, filed on Aug. 1, 2014.

(51) Int. Cl.
| | | |
|---|---|---|
| C07C 315/02 | (2006.01) | |
| C07C 315/04 | (2006.01) | |
| C07C 319/14 | (2006.01) | |
| C07C 319/20 | (2006.01) | |
| B01J 31/02 | (2006.01) | |

(52) U.S. Cl.
CPC ......... *C07C 315/02* (2013.01); *B01J 31/0244* (2013.01); *C07C 315/04* (2013.01); *C07C 319/14* (2013.01); *C07C 319/20* (2013.01); *B01J 2231/40* (2013.01); *B01J 2531/002* (2013.01)

(58) Field of Classification Search
None
See application file for complete search history.

(56) References Cited

U.S. PATENT DOCUMENTS 7,531,694 B2    5/2009  Villa et al.

OTHER PUBLICATIONS

Bracci Torsi, "Su alcuni nuovi derivati analoghi alla carbutammide", Gazzetta Chimica Italiana, 1960, vol. 90, pp. 1658-1966, XP008086526.
National Center for Biotechnology Information,Database Accession No. 24215273, Compound No. 24215273, 2008, pp. 1-10, XP002743431.
Gannett, et al., "Synthesis of deuterated 4, 4-diaminodiphenylsulfone (Dapsone) and related analogs", Journal of Labelled Compounds and Radiopharmaceuticals, 2003, vol. 46, No. 2, pp. 107-114, XP002743432.
Clark, et al., "Discovery and SAR development of 2-(phenylamino) imidazolines as prostacyclin receptor antagonists", Bioorganic & Medicinal Chemistry Letters, 2004, vol. 14, No. 4, pp. 1053-1056, XP002303260.
Meyer, "Zur Kenntnis der aromatischen Sulfosaeuren Und Sulfone", Justus Liebigs Annalen Der Chemie, 1923, vol. 433, pp. 327-350, XP002025422.
International Search Report and Written Opinion for International Application No. PCT/EP2015/067411 (9 pages) (dated Sep. 15, 2015).

*Primary Examiner* — Clinton Brooks
(74) *Attorney, Agent, or Firm* — Lucas & Mercanti, LLP

(57) ABSTRACT

A process for the synthesis of Dapsone and intermediates thereof are described.

16 Claims, No Drawings

PROCESS FOR THE SYNTHESIS OF DAPSONE AND ITS INTERMEDIATES

CROSS-REFERENCE TO RELATED APPLICATIONS

This application is a 371 of PCT/EP2015/067411, filed Jul. 29, 2015, which claims the benefit of the U.S. Provisional Application No. 62/032,154, filed Aug. 1, 2014.

FIELD OF THE INVENTION

The present invention refers to a process for the synthesis of Dapsone, and to intermediates for its preparation.

BACKGROUND OF THE INVENTION

Dapsone (diamino-diphenyl sulfone) is an antibacterial most commonly used in combination with rifampicin and clofazimine as multidrug therapy (MDT) for the treatment of *Mycobacterium leprae* infections (leprosy).

Leprosy is a contagious infectious disease with a chronic course and generally with fatal outcome; it is also known as Hansen's Disease (HD), from the Norwegian physician who first isolated the pathogen in *Mycobacterium leprae.*

The most common transmission is by direct interpersonal infection or mediated by insects, especially arthropods.

An incubation period (from 1-2 to 30 years) is followed by a period of invasion that is often associated with general symptoms, such as fever, headache, epistaxis, and neuralgic pains.

In a third time the characteristic manifestations of one of three forms appear: tuberculoid leprosy, lepromatous leprosy and mixed leprosy.

The tuberculoid leprosy is characterized by the appearance on the skin and viscera of nodules of various volume, isolated or confluent and that can be reabsorbed, thus leaving as aftermath white patches as atrophic or pigmented or ulcerated.

In lepromatous leprosy eruptions of bubbles (pemphigus leprosum), achromic anesthetic belmishes, gangrenes, areas of anesthesia "strip", "boot" or "sleeve" anesthesia can appear. In the mixed leprosy can prevail one or the other form. Death occurs, after a course of variable length, for cachexia or kidney, lung, or other organs problems.

Dapsone is a sulfonamide used against leprosy since the Second World; it has a bacteriostatic action, due to its ability to substitute para-aminobenzoic acid (PABA), which becomes part of the structure of folic acid. Because of its replacement with the sulfonamide, the bacterial dihydropteroate synthetase, which is an enzyme present in bacteria and protozoa but absent in humans and that catalyzes the incorporation of PABA into the dehydrofolic acid, it can no longer synthesize the latter, with consequent stop of the bacterial multiplication.

Therefore, Dapsone acts as an antimetabolite, but it does not kill the bacteria, so that the patients were cured for all life long.

Combination chemotherapy (namely, the combined use of two or three drugs—Rifampicin, Clofazimine and Dapsone) continues to be the most important treatment of leprosy in the world; initial treatment lasted for periods varying from 1 to 3 years or more, but nowadays the duration of treatment has been reduced and varies from 6 to 12 months.

Dapsone is also used in the treatment of dermatological diseases; in this case, its pharmacodynamics has not yet been well understood. Certainly, it appears to have anti-inflammatory and immunomodulatory effects.

Dapsone is a compound of formula (I)

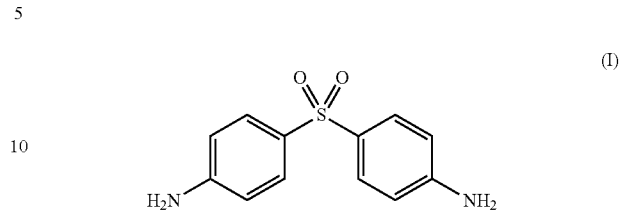

chemically known as 4,4'-diamino-diphenyl sulfone, described in FR 829 926 and marketed under the name of Aczone®.

FR 829.926 discloses a process for the synthesis of Dapsone, as reported in Scheme 1:

Scheme 1

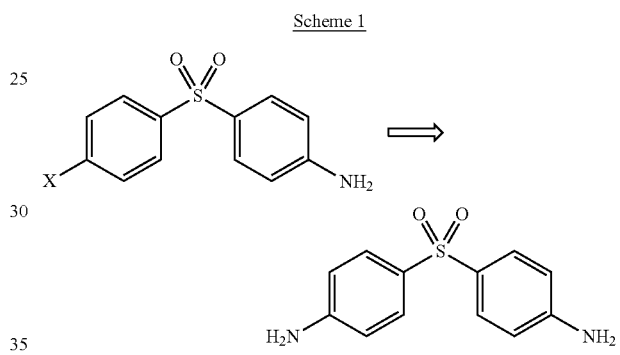

which is carried out in the presence of ammonia or an agent comprising ammonia or organic amines comprising at least one hydrogen atom bound to N, and wherein X is halogen.

U.S. Pat. No. 7,531,694 discloses a process for the synthesis of Dapsone, as reported in Scheme 2:

Scheme 2

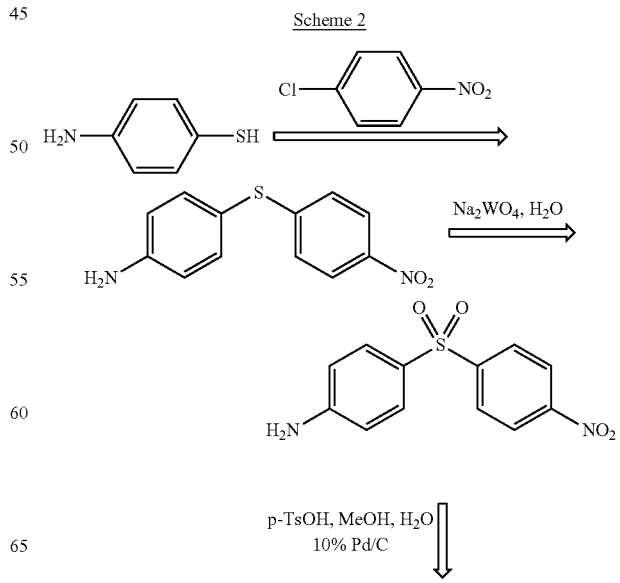

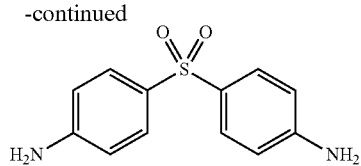

U.S. Pat. No. 6,998,490 discloses a process for the synthesis of Dapsone, as reported in Scheme 3:

Scheme 3

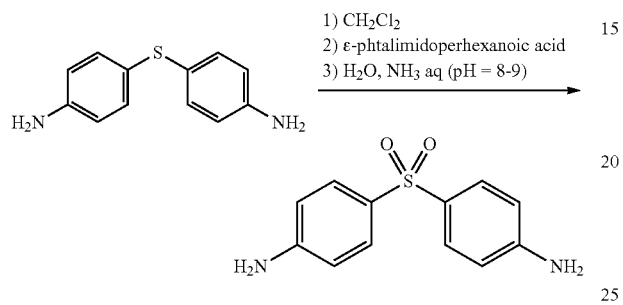

SUMMARY OF THE INVENTION

The present invention refers to a process for the synthesis of Dapsone and to its intermediates as per the appended set of claims.

DETAILED DESCRIPTION OF EMBODIMENTS OF THE INVENTION

The present invention refers to a process for the synthesis of Dapsone comprising the following steps:

a) a condensation reaction between a compound of formula (II)

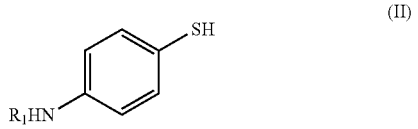

(II)

with a compound of formula (III)

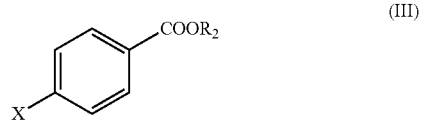

(III)

to give a compound of formula (IV)

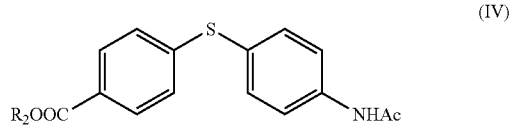

(IV)

wherein:

$R_1$ is selected from the group consisting of H atom and an acetyl group;

X is selected from the group consisting of F, I, Cl and Br, preferably, X is F; and $R_2$ is selected from the group consisting of a linear $C_{1-10}$ alkyl and a branched $C_{1-10}$ alkyl, preferably, $R_2$ is methyl;

b) b.i)—the oxidation reaction to sulfone of a compound of formula (IV), to give a compound of formula (V)

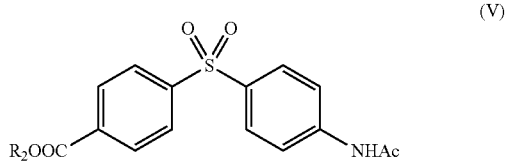

(V)

the hydrolysis reaction of a compound of formula (V), to give a compound of formula (VI)

or

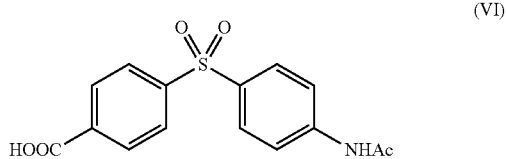 [SMILES: CC(=O)Nc1ccc(S(=O)(=O)c2ccc(C(=O)O)cc2)cc1]

(VI)

b.ii)—a saponification reaction of the compound of formula (IV) to give the compound of formula (XIII)

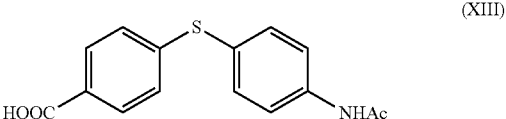 [SMILES: CC(=O)Nc1ccc(Sc2ccc(C(=O)O)cc2)cc1]

(XIII)

and an oxidation reaction to sulfone of the compound of formula (XIII) to give the compound of formula (VI);

c) the conversion of the compound of formula (VI) into the corresponding hydroxamic acid of formula (VII)

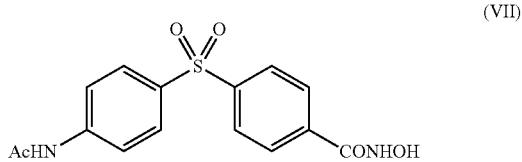

(VII)

d) the Lossen rearrangement reaction of the compound of formula (VII) to give the compound of formula (VIII)

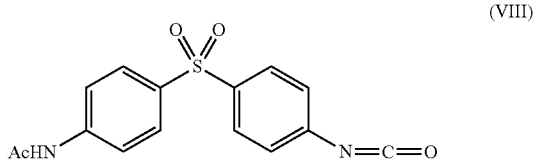 [SMILES: CC(=O)Nc1ccc(S(=O)(=O)c2ccc(N=C=O)cc2)cc1]

(VIII)

e) the reaction of the compound of formula (VIII) with:
an alcohol to give a compound of formula (IX)

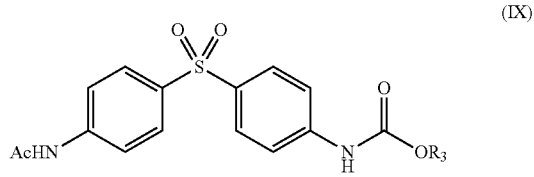

(IX)

wherein
$R_3$ is selected from the group consisting of a $C_{1-10}$ linear alkyl and a $C_{1-10}$ branched alkyl, preferably $R_3$ is allyl;
or
with water to give the compound of formula (X)

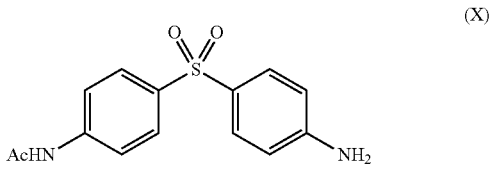 [SMILES: CC(=O)Nc1ccc(S(=O)(=O)c2ccc(N)cc2)cc1]

(X)

f) the conversion of compound (IX) or (X) into Dapsone.

The step a) of the process object of the present invention is carried out in the presence of a base in an aprotic polar solvent.

The base is selected from the group consisting of potassium carbonate and cesium carbonate, preferably, the base is potassium carbonate.

The aprotic polar solvent is selected from the group consisting of dimethylsulfoxide, acetonitrile, and N,N-dimethylformamide; preferably, the aprotic polar solvent is dimethylsulfoxide.

When $R_1$ represents a hydrogen atom, a compound of formula (IVa) is obtained

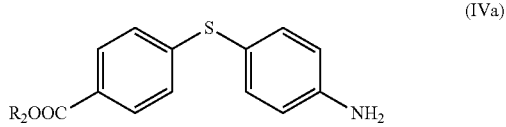

(IVa)

wherein $R_2$ has the above reported meanings.

The compound of formula (IV) is then obtained by an acetylation reaction of the amino group with acetic anhydride, in the presence of a catalytic amount of an amine, such as 4-dimethylaminopyridine (DMAP), in an apolar solvent selected from the group consisting of hexane, toluene, ethyl acetate, dimethyl sulfoxide, and tetrahydrofuran; preferably, the apolar solvent is toluene.

The oxidation reactions of steps b.i) and b.ii) of the process object of the present invention are carried out with a compound selected from the group consisting of sodium perborate, which is the preferred embodiment, sodium hypochlorite, and sodium percarbonate, in a protic polar solvent and, optionally, in the presence of a compound selected from the group consisting of trichloroisocyanuric acid (TCCA), succinimide, acetamide and cyanuric acid.

The protic polar solvent is selected from the group consisting of acetic acid, alcohols and a mixture of polar solvents selected from the group consisting of water, alcohols and an apolar solvent selected from toluene, hexane, ethyl acetate, dimethyl sulfoxide, preferably a mixture of water and toluene; preferably, the protic polar solvent is acetic acid. Preferably, sodium perborate in acetic acid is used.

The hydrolysis reaction of step b.i) and the saponification reaction of step b.ii) of the process object of the present invention are carried out in the presence of a base in a suitable solvent. The base is selected from the group consisting of sodium hydroxide, potassium hydroxide, and lithium hydroxide; preferably, the base is sodium hydroxide.

The solvent is a mixture of water and a solvent selected from the group consisting of toluene, hexane, ethyl acetate, dimethyl sulfoxide, tetrahydrofuran and alcohols, such as methanol, ethanol, isopropanol and butanol. Preferably, a mixture of tetrahydrofuran and water is used.

The step c) of the process object of the present invention is carried out by reaction with hydroxylamine hydrochloride, in the presence of a condensing agent in a polar aprotic solvent. The condensing agent is selected from carbonyldiimidazolo (CDI), dicyclohexylcarbodimide (DCC), N-ethylcarbodimide hydrochloride (EDC.HCl), 2,4,6-tri-n-propyl-2-1,4,6-trioxo,3,5,2,4,6-trioxo-triphosphorinane (T3P®)), preferably carbonyldiimidazole (CDI). The aprotic polar solvent is selected from the group consisting of acetone, acetonitrile, N,N-dimethylformamide, and dimethyl sulfoxide; preferably the aprotic polar solvent is acetonitrile.

Preferably, the step c) of the process object of the present invention is carried out by reaction with hydroxylamine hydrochloride, in the presence of carbonyldiimidazole in acetonitrile.

Alternatively, the hydroxamic acid can be obtained directly from the compound of formula (VI) by treatment with hydroxylamine.

In the step d) of the process of the present invention, the Lossen rearrangement reaction can be carried out by means of O-activation of the hydroxaminic acid of formula (VII) by reaction of anhydrides, acyl halides ($R_4COCl$), $R_4SO_2Cl$ or$R_4PO_2Cl$;
wherein $R_4$ is selected from the group consisting of a linear $C_{1-10}$ alkyl, branched $C_{1-10}$ alkyl, an optionally substituted aryl group, such as p-nitrobenzensolfonyl chloride, tionylchlorid, SO3*$Et_3$N, dialkyl-carbodimides, activated aromatic halides (eg. 2,4-dinitrochlorobenzene), silylating agents, carbonyldiimidazole (CDI).

Then, a reaction with a base is followed, wherein the base is selected from the group consisting of sodium hydroxide, potassium hydroxide, 1,5-diazabicyclo (5.4.0) undec-5-ene (DBU), N, N,-diisopropylethylamine (DIPEA), triethylamine (TEA), tributylamine, in the presence of an aromatic amine catalyst, such as 4-dimethylaminopyridine (DMAP), in a polar aprotic solvent selected from the group consisting of dimethylsulfoxide, acetonitrile, N, N-dimethylformamide, preferably acetonitrile.

Preferably, the step d) is carried out in the presence of p-nitrobenzylsolfonyl chloride, N, N-diisopropylethylamine (DIPEA) and catalytic 4-dimethylaminopyridine (DIMAO), in acetonitrile.

In step e) of the process of the present invention, the alcohol is selected from the group consisting of allyl alcohol, ter-butanol, benzyl alcohol, isopropanol, n-butanol, preferably, the alcohol is allyl alcohol.

Alternatively, the compound of formula (X) is obtained by reacting the isocyanate of formula (VIII) with water.

In step f) of the process of the present invention, Dapsone is directly obtained from the compound of formula (IX) or from the compound of formula (X) by known deprotection methods of the functional groups. Preferably, the deprotection is carried out with acidic water.

The compounds of formula (IV), (V), (VI), (VII), (IX), are new intermediates which are useful in the Dapsone synthesis and they represent another object of the present invention.

Although the invention has been described in its characteristic aspects, modifications and equivalents that are apparent to the person skilled in the art are included in the following invention.

The present invention will now be illustrated by means of some examples, which should not be viewed as limiting the scope of the invention.

All terms used in this application, unless otherwise stated, are to be understood in their common meaning as known in the art.

Other more specific definitions for certain terms as used in this application, are highlighted below and apply consistently throughout the specification and claims, unless a different definition explicitly provides a broader definition.

Example 1

Synthesis of methyl 4-(4-amino-phenyl-thio)benzoate

In a reaction flask 9.00 g of methyl4-methyllfluorobenzoate (0.058 mol), 6.88 g of 4-aminothiophenol (0.055 mol), 55 ml of dimethyl sulfoxide, 8.43 g of potassium carbonate (0.061 mol) were charged, and the reaction mixture was left at a temperature of about 25° C. for about two hours.

At the end of the reaction, 200 ml of toluene were added in 200 ml of a saturated solution of sodium chloride, and the aqueous phases were extracted with toluene (1×140 ml). The combined organic phases were reduced to a residue by vacuum distillation to give 3.6 g of methyl4-(4-aminophenylthio) benzoate.

Example 2

Synthesis of methyl 4-(4-acetamidophenyl thio)benzoate

In a reaction flask 3.6 g of methyl 4-(4-aminophenylthio) benzoate (0.014 mol), 24 ml of acetonitrile, 0.085 g of 4-dimethylaminopyridine (DMAP 0.007 mol), and, dropwise, 1.73 g of acetic anhydride (0.017 mol) were charged. The reaction mixture was left under stirring for about 1 hour.

At the end of the reaction, the temperature was brought to 15° C., and thus the resulting solid was cold filtered with 4 ml of acetonitrile and then dried in a vacuum drying oven at 38° C. to give 3.4 g of methyl 4-(4-acetamidophenylthio) benzoate.

Example 3

Synthesis of methyl 4-(4-acetamidophenylsulfonyl)benzoate

In a reaction flask 3.2 g of methyl 4-(4-acetamidophenylthio)benzoate (0.0106 mol), 32 ml of acetic acid, 5.3 g of sodium perborate (0.053 mol) were charged, the temperature was brought to about 45° C. and the reaction mixture was left for about 1.5 hours in these conditions.

At the end of the reaction, the temperature was brought to 25° C., and then 40 ml of ethyl acetate and 35 ml of water were charged; the aqueous phase was extracted with ethyl acetate (1×20 ml) and the organic phase was washed with a saturated solution of sodium bicarbonate (2×60 ml).

The resulting product was filtered and dried in a vacuum drying oven at 45° C., to give 3.5 g of methyl 4-(4-acetamidophenylsulfonyl)benzoate.

Example 4

Synthesis of methyl 4-(4-acetamidophenylsulfonyl)benzoate

In a reaction flask 0.100 g of methyl 4-(4-acetamidophenylthio)benzoate (0.0003 mol), 2 ml of toluene, 0.007 g of trichloroisocyanuric acid (TCCA, 0.00003 mol) and 0.0560 g of an aqueous solution of sodium ipochlorite at 12% (0.0009 mol) were charged. The reaction mixture was left under stirring for 2 hours.

At the end of the reaction, 3 ml of ethyl acetate and 2 ml of water were added; the aqueous phase was extracted with ethyl acetate (1×5 ml) and the collected organic phase was washed with a saturated solution of sodium bicarbonate (2×5 ml).

The resulting product has been filtered and then dried in a vacuum drying oven at 45° C., to give 0.080 g of methyl 4-(4-acetamidophenylsulfonyl)benzoate.

Example 5

Synthesis of 4-(4-acetamidophenylsulfonyl)benzoic acid

In a reaction flask 2.1 g of methyl 4-(4-acetamidophenylenilsulfonyl)benzoate (0.0062 mol), 10.5 ml of tetrahydrofuran, 3.6 ml of water, 0.907 g of sodium hydroxide at 30% (0.0068 mol) were charged, the temperature was brought at 30° C., and the reaction mixture was left under stirring for about 2 hours.

At the end of the reaction, the temperature was brought to 25° C., and 18 ml of toluene and 12 ml of water were added. The aqueous phase was extracted with toluene (1×10 ml) and a 2 N solution of hydrochloric acid was added to reach a pH value of 1. The resulting solid was filtered and washed with water (2×3 ml) and then dried in a vacuum drying oven at 48° C. to give 3.9 g of 4-(4-acetamidophenylsulfonyl) benzoic acid.

Example 6

Synthesis of 4-(4-acetamidophenylsulfonyl)-N-hydroxybenzenamide

In a reaction flask 0.300 g of 4-(4-acetamidophenylsulfonyl)benzoic acid (0.001 mol), 3 ml of acetonitrile, 0.195 g of carbonylimidazole (CDI, 0.0012 mol) and 0.087 g of hydroxylamine hydrochloride (0.0013 mol) were charged. The reaction mixture was left at room temperature for about 4 hours.

At the end of the reaction, the solvent was removed by vacuum distillation and were added 3 ml of water, 5 ml of ethyl acetate and the pH was brought to a value of about 1 using hydrochloric acid solution 2 N. The collected organic phases were reduced to a residue by distillation under vacuum to give 0.250 g of 4-(4-acetamidophenylsulfonyl)-N-hydroxybenzamide.

Example 7

Synthesis of allyl 4-(4-acetammidophenylnilsulfonyl)-phenylcarbammate

In a reaction flask 0.200 g of 4-(4-acetamidophenylsulfonyl)-N-hydroxybenzamide (0.0006 mol), 3.5 ml di tetrahydrofuran, 0.194 g of N,N-diisopropylethylamine (DIPEA, 0.0015 mol) were charged, the temperature was brought to about 0° C., 0.146 g of p-nitro-benzen-sulfonyl chloride were added (0.0007 mol), and the reaction mixture was left in these conditions for about 2.5 hours.

At the end of the reaction, the temperature was brought to about 25° C., and then 0.015 g of 4-dimethylaminopyridine (DMAP, 0.0001 mol), 0.070 g of allyl-alcohol (0.0012 mol) were added and the reaction mixture was left under these conditions for about three hours.

At the end of the reaction, 15 ml of ethyl acetate and 8 ml of water were added and the aqueous phase was extracted with ethyl acetate (1×6 ml). The organic phase was washed with a 2 N solution of hydrochloric acid (1×5 ml), water (1×5 ml) and a saturated solution of sodium bicarbonate (1×12 ml). The collected organic phases were purified by column chromatography, to give 0.080 g of allyl 4-(4-acetamidophenylsulfonyl)-phenylcarbamate.

Example 8

Synthesis of N-(4-(4-aminophenylsulfonyl) phenyl) acetamide

In a reaction flask 0.030 g of allyl 4-(4-acetammidophenylsulfonyl)-phenylcarbamate (0.00008 mol), 2.5 ml of methanol, 0.001 g of tetrakis(triphenylphosphine)palladium (0) (0.0000008 mol), 0.070 g of potassium carbonate (0.0005 mol) were charged, and the reaction mixture was kept at a temperature of 25° C. for about twelve hours.

At the end of the reaction, 3 ml of methyl ethyl ketone and 1.5 ml of water were added, the aqueous phase was extracted with methyl ethyl ketone (2×2 ml) and the combined organic phases were reduced to a residue by distillation under vacuum, to give 10 mg of N-(4-(4-aminophenylsulfonyl) phenyl) acetamide.

Example 9

Synthesis of 4-(4-acetamidophenylsulfonyl) benzoic acid

In a reaction flask 0.300 g of 4-(4-acetamidophenylthio) benzoic acid (0.0011 mol), 4 ml of acetic acid, 0.550 g of sodium perborate (0.0055 mol) were charged, the temperature was raised to about 45° C. and the reaction mixture was kept under these conditions for about an hour.

At the end of the reaction, the formed solid was hot filtered, washed with water (2×1.5 ml) and dried in a vacuum drying oven at 45° C. to give 0.200 g of 4-(4-acetamidophenylsulfonyl) benzoic acid.

Example 10

Synthesis of 4-(4-acetamidophenylthio)benzoic acid

In a reaction flask 9.7 g of methyl 4-methylfluorobenzoate (0.063 mol), 10 g of acetamidothiophenol (0.060 mol), 50 ml of dimethylsulfoxide and 1.04 g of 1,5-diazabicyclo (5.4.0)undec-5-ene (DBU, 0.007 mol) were charged and the reaction was kept under stirring for about 3 hours.

At the end of the reaction, 16.6 g of potassium carbonate, 3 ml of a solution of sodium hydroxide at 30% were added, and the temperature was brought to about 55° C. and the reaction was kept under these conditions for about 3 hours.

At the end of the reaction, the temperature was brought to about 15° C., and then 200 ml of water and a solution of hydrochloric acid at 37% up to a pH value of 1 were added. The precipitated solid was filtered and washed to give 12.1 g of 4-(4-acetamidophenylthio)benzoic acid.

Example 11

Synthesis of Dapsone

In a reaction flask 10 mg of N-(4-(4-aminophenylsulfonyl)phenyl)acetamide (0.00008 mol), 2 ml di methanol, 1 ml of water and 6 mg of NaOH (0.00016 mol) were charged, the temperature was brought to about 35° C. and the reaction mixture was kept under in these conditions for about 2 hours.

At the end of the reaction, 2 ml of ethyl acetate were added, the aqueous phase was extracted with ethyl acetate (1×1 ml), and the collected organic phases were reduced to a residue by distillation under vacuum to give 5 mg of Dapsone.

The invention claimed is:

1. A process for the synthesis of Dapsone comprising the following steps:
   a) a condensation reaction between a compound of formula (II)

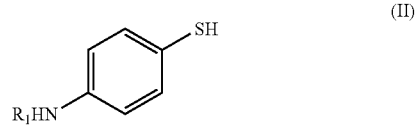

with a compound of formula (III)

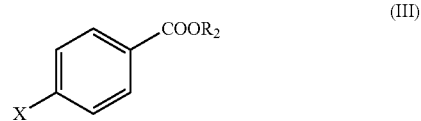

to give a compound of formula (IV)

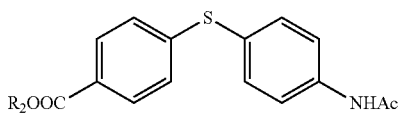

in the presence of a base in an aprotic polar solvent, and a catalytic amount of an amine in apolar solvent;
wherein:
$R_1$ is selected from the group consisting of H atom and an acetyl group,
X is selected from the group consisting of F, I, Cl and Br,
and
$R_2$ is selected from the group consisting of a linear $C_{1-10}$ alkyl and a branched $C_{1-10}$ alkyl;
b) b.i)—the oxidation reaction to sulfone of a compound of formula (IV), to give a compound of formula (V)

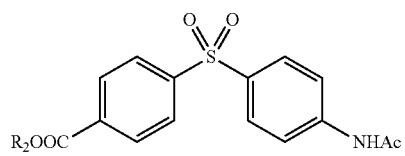

and
the hydrolysis reaction of a compound of formula (V) to give a compound of formula (VI)

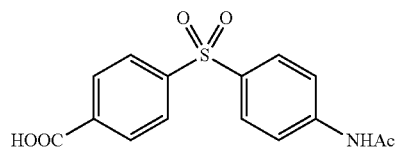

in the presence of a base in a solvent;
or
b.ii)—a saponification reaction of the compound of formula (IV) to give the compound of formula (XIII)

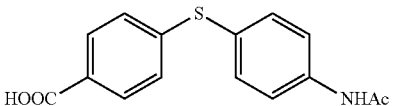

in the presence of a base in a solvent
and
an oxidation reaction to sulfone of the compound of formula (XIII) to give the compound of formula (VI);
c) the conversion of the compound of formula (VI), into the corresponding hydroxamic acid of formula (VII)

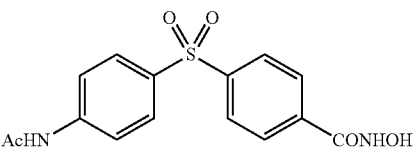

by reaction with hydroxylamine hydrochloride, in the presence of a condensing agent in a polar aprotic solvent;
d) the Lossen rearrangement reaction of the compound of formula (VII) to give the compound of formula (VIII)

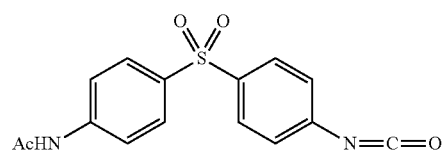

e) the reaction of the compound of formula (VIII) with:
an alcohol to give a compound of formula (IX)

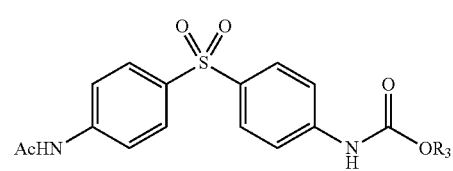

wherein
$R_3$ is selected from the group consisting of a $C_{1-10}$ linear alkyl and a $C_{1-10}$ branched alkyl;
or
with water to give the compound of formula (X)

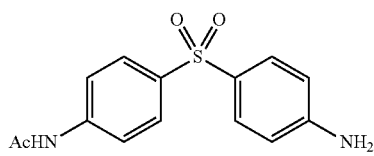

f) deprotection of the functional groups of compound of formula (IX) or (X) to give Dapsone.

2. The process according to claim 1) wherein in step a) the base is selected from the group consisting of potassium carbonate and cesium carbonate.

3. The process according to claim 1) wherein in step a) the aprotic polar solvent is selected from the group consisting of dimethylsulfoxide, acetonitrile, and N,N-dimethylformamide.

4. The process according to claim 1) wherein in step a) the catalytic amount of an amine is 4-dimethylaminopyridine.

5. The process according to claim 1, wherein in step a) the apolar solvent is selected from the group consisting of hexane, toluene, ethyl acetate, dimethyl sulfoxide, and tetrahydrofuran.

6. The process according to claim 1, wherein the oxidation reaction in steps b.i) and b.ii) is carried out with a compound selected from the group consisting of sodium perborate, sodium hypochlorite, and sodium percarbonate, in a protic polar solvent, optionally in the presence of a compound selected from the group consisting of trichloroisocyanuric acid, succinimide, acetamide and cyanuric acid.

7. The process according to claim 6, wherein the protic polar solvent is selected from the group consisting of acetic, alcohols and a mixture of polar solvents selected from the group consisting of water, alcohols and an apolar solvent selected from toluene, hexane, ethyl acetate, dimethyl sulfoxide.

8. The process according to claim 1 wherein in step b.i) and step b.ii) the base is selected from the group consisting of sodium hydroxide, potassium hydroxide, and lithium hydroxide.

9. The process according to claim 1, wherein in step b.i) and b.ii) the solvent is a mixture of water and a solvent selected from the group consisting of toluene, hexane, ethyl acetate, dimethyl sulfoxide, tetrahydrofuran and alcohols selected from the group consisting of methanol, ethanol, isopropanol and butanol.

10. The process according to claim 1, wherein in step c) the condensing agent is selected from the group consisting of carbonyldiimidazole, dicyclohexylcarbodimide, N-ethylcarbodimide hydrochloride, 2,4,6-tri-n-propyl-2-1,4,6-tri-oxo,3,5,2,4,6-trioxo-triphosphorinane.

11. The process according to claim 1, wherein in step c) the aprotic polar solvent is selected from the group consisting of acetone, acetonitrile, N,N-dimethylformamide, and dimethyl sulfoxide.

12. The process according to claim 1, wherein step c) is carried out by reaction with hydroxylamine hydrochloride, in the presence of carbonyldiimidazole in acetonitrile.

13. The process according to claim 1, wherein in step d) the Lossen rearrangement reaction is carried out
by means of O-activation of the hydroxyl-aminic acid of formula (VII) by reaction of anhydrides, acyl halides, $R_4COCl$, $R_4SO_2Cl$, $R_4PO_2Cl$; and
by a reaction with a base in the presence of an aromatic amine catalyst in a polar aprotic solvent;
wherein:
$R_4$ is selected from the group consisting of a linear $C_{1-10}$ alkyl, branched $C_{1-10}$ alkyl, an optionally substituted aryl group selected from the group consisting of p-nitrobenzensolfonyl chloride, thionylchloride, $SO_3*Et_3N$, dialkyl-carbodimmides, activated aromatic halides, silylating agents, and carbonyldiimidazole;
the base is selected from the group consisting of sodium hydroxide, potassium hydroxide, 1,5-diazabicyclo(5.4.0)undec-5-ene, N,N,-diisopropylethylamine, triethylamine, tributylamine,
the polar aprotic solvent is selected from the group consisting of dimethylsulfoxide, acetonitrile, and N,N-dimethylformamide.

14. The process according to claim 1, wherein step d) is carried out in the presence of p-nitrobenzylsolfonyl chloride, N,N-diisopropylethylamine and catalytic 4-dimethylamminopyridine, in acetonitrile.

15. The process according to claim 1, wherein in step e) the alcohol is selected from the group consisting of allyl alcohol, ter-butanol, benzyl alcohol, isopropanol, n-butanol.

16. The process according to claim 1, wherein the step e) the compound of formula (X) is obtained by reacting isocyanate of formula (VIII) with water.

* * * * *